United States Patent [19]
Rhoads et al.

[11] 4,120,305
[45] Oct. 17, 1978

[54] SYSTEM FOR ADMINISTERING AN ELECTRIC SHOCK

[75] Inventors: Kevin George Rhoads, Lehighton, Pa.; George Michael Plotkin, Massapequa Pk., N.Y.

[73] Assignee: VRL Growth Associates, Inc., Boston, Mass.

[21] Appl. No.: 722,313

[22] Filed: Sep. 10, 1976

[51] Int. Cl.$^2$ ............................................. A61N 1/38
[52] U.S. Cl. ................... 128/405; 128/419 S; 128/422; 231/2 E; 273/84 ES; 361/232
[58] Field of Search ............. 128/405, 404, 410, 411, 128/419 S, 419 R, 422; 231/2 E; 272/27 R, 27 N; 273/84 ES; 361/232

[56] References Cited

U.S. PATENT DOCUMENTS

| | | | |
|---|---|---|---|
| 2,473,378 | 6/1949 | Liberson | 128/419 S |
| 3,025,858 | 3/1962 | Browner | 128/422 |
| 3,295,528 | 1/1967 | Masaki | 128/422 |
| 3,362,711 | 1/1968 | Larsen et al. | 273/84 ES |
| 3,608,524 | 9/1971 | Waltz | 231/2 E X |
| 3,722,788 | 3/1973 | Petrecz | 273/84 ES X |
| 3,881,495 | 5/1975 | Pannozzo et al. | 128/422 |
| 3,889,163 | 6/1975 | Symmes | 361/232 |
| 3,917,268 | 11/1975 | Tingey et al. | 273/84 ES |
| 3,998,459 | 12/1976 | Henderson et al. | 273/84 ES |
| 4,014,347 | 3/1977 | Halleck et al. | 128/422 |
| 4,018,218 | 4/1977 | Carlson et al. | 128/422 X |

FOREIGN PATENT DOCUMENTS

| | | | |
|---|---|---|---|
| 1,507,930 | 4/1971 | Fed. Rep. of Germany | 361/232 |
| 256,744 | 1/1928 | Italy | 361/232 |
| 1,339,419 | 12/1973 | United Kingdom | 231/2 E |

OTHER PUBLICATIONS

Webber, "A Simple Battery-Powered Stimulator . . . Therapy", Med. & Biol. Eng., vol. 6, pp. 445–446, 1968.

*Primary Examiner*—Lee S. Cohen
*Attorney, Agent, or Firm*—Jim Zegeer

[57] ABSTRACT

There is disclosed a self-protective system for administering an electrical shock to a would-be assailant by first establishing a low resistance path to the nervous system of the assailant and then coupling thereto an interference signal voltage having a frequency within the passband of the nerves. It incorporates a novel compact power oscillator which is normally quiescent until applied to a load, to produce, under load, a waveform which has a unique application to self-protective devices and medical uses. The oscillator includes a high gain inverting amplifier, preferably a Darlington pair constituted by a germanium output transistor driven by a small signal transistor, a transformer, a D.C. source such as a battery, and a pair of output electrodes.

32 Claims, 6 Drawing Figures

FIG 3(A) LOADED

FIG 3(B) UNLOADED

T = PERIOD OF FUNDAMENTAL
$V_{pL}$ = PEAK VOLTAGE
$V_{AVE}$ = AVERAGE VOLTAGE

✻ NORMALLY FOUR BUT OCCASIONALY FIVE OR SIX LOCAL MAXIMA WERE OBSERVED IN THIS AREA OVER A WIDE RANGE OF CONDITIONS WITH VARIOUS PROTOTYPE CIRCUIT ELEMENTS.

SYSTEM FOR ADMINISTERING AN ELECTRIC SHOCK

BACKGROUND OF THE INVENTION

The present invention relates to a personal defense system for administering an electrical shock to a would-be assailant. Such devices are well known in the art as is exemplified by Creedon U.S. Pat. No. 1,046,985 in an early form, and in Cover U.S. Pat. No. 3,083,463 in a more recent form, the latter patent dealing in some detail with the nature of electrical currents on the human body. Still more recently, Tingley et al. U.S. Pat. No. 3,917,268 discloses a particular form of relaxation oscillator in which a spark gap is used to isolate the load from the oscillator circuit per se. These patents, as well as many, many others, disclose various forms of oscillator circuits, particularly adaptable to use in applying various forms of electrical energy to the human body or animals, either for self-protection purposes or for medical treatment purposes. Some of these prior art oscillator circuits, such as Browner U.S. Pat. No. 3,025,858 utilize as a part of the oscillatory circuit the portion of the human body between the electrodes; others, such as Moss et al. U.S. Pat. No. 3,180,338 use a separate output circuit to the load electrodes. However, such devices as disclosed in the Browner patent, for example, require that the electrodes be wetted with water before the device is placed in operation which, manifestly, is unacceptable when used in connection with a self-protection system. Other systems are relatively complex and require critical component selection and/or adjustment, are more expensive and do not provide output waveforms of the type disclosed herein for the unique and novel practices of this invention.

THE PRESENT INVENTION

In accordance with the present invention, a normally quiescent oscillatory circuit is provided which includes a high gain inverting amplifier which, in a highly preferred embodiment, is a Darlington connected transistor pair with a germanium type PNP output transistor, an inverting transformer element for providing, by transformer action, a stepped up voltage, a power supply which, in the preferred embodiment, is a small direct current battery, and a pair of output electrodes, one of which is connected to the input base electrode of the Darlington pair and the other of which is connected to the secondary winding portion of the transformer. Normally, in the absence of a resistance, such as a portion of the body, across the output electrodes, the circuit is normally quiescent with the only power consumed being the leakage current between the collector-emitter electrodes of the output transistor, the input base electrode being, effectively, open circuited.

Immediately upon the presence of the body portion across the output electrodes, a small signal current is developed and applied to the base electrode of the input transistor of the Darlington pair, which by virtue of the high current gain of the Darlington pair is amplified and applied as a current pulse to the transformer primary via the collector-emitter circuit of the output power transistor of the Darlington pair. This current pulse induces a high voltage in the secondary winding of the transformer which, through feedback action, is applied through the body portion in contact with the electrode pair as an input to the base electrode of the input transistor of the Darlington pair which is amplified so that the process continues to repeat itself until the saturation occurs.

This action induces a rather large voltage pulse which is followed by a lower sequence of oscillatory pulses. Thus, the circuit generates, under load, a waveform which, in connection with a self-protection device as described above, breaks down the skin resistance and then couples directly into the sensory nerves, via this transient relatively lower resistance path, a signal within the passband of the nerves. Advantages of the invention are that lower power is used, the circuit remains in a quiescent state, consuming extremely small amounts of power. An important feature of the invention is that adjustment of the circuit is not critical at all and as the loading is increased or a lower body resistance is applied or appears at the terminals of the electrode, the power increases. Thus, the circuit also adapts itself to the load.

The above and other objects, advantages and features of the invention will become more apparent from the following specification taken in conjunction with the accompanying drawings wherein:

DESCRIPTION OF THE DRAWINGS

FIGS. 3(A), 3(B) and 3(C) are illustrations of the preferred form of the waveform which includes one or more large voltage pulses for breaking down the skin resistance of an assailant and then coupling into the sensory nerves of such assailant a relatively lower amplitude voltage signal which disables such assailant.

Referring now to FIG. 1, the block diagram illustrates a power supply 10 connected via a pair of leads 11 and 12 and a switch 13 to voltage conditioning circuit 14 which has a pair of output electrodes 15 and 16 connected to the output terminals thereof. The switch 13 is diagrammatically illustrated as having an operating element 17 associated with the electrodes 15 and 16 so that power is not supplied to the oscillator circuit until, for example, an assailant is across or in contact with both electrodes 15 and 16 (primed in FIGS. 2 and 4). Of course, such a safety feature may be deleted if desired.

Figure 1:
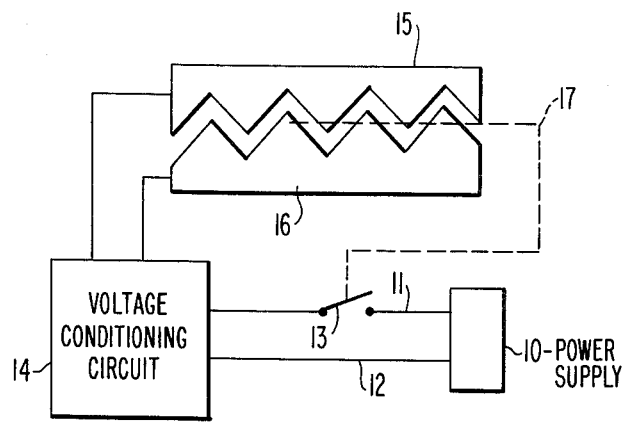
FIG. 1 is a block diagram of a circuit incorporating the invention.

In its most highly preferred form, the oscillator 14 is constituted by an inverting amplifier which is, preferably, a saturating Darlington-connected PNP transistor pair Q1 and Q2. Collector 21 of transistor Q1 and collector 22 of transistor Q2 are commonly connected together and to terminal 23 of primary winding 24 on inverting transformer 20. Terminal 25 of primary winding 24 is connected to negative terminal 26 of a direct current power supply 27 which, in turn, has its positive terminal or pole 28 connected to emitter 29 of transistor $Q_2$. Base 30 of transistor Q2 is directly connected to emitter 31 of transister Q1. Base 32 of transistor Q1 is connected by a lead 33 to an output load terminal 34 whereas a second output load terminal 35 is connected by a lead 36 to terminal 37 of secondary winding 38 of transformer 20. It will be noted that the primary winding 24 and secondary winding 38 of transformer 20 have the polarity relationships indicated by the dots at the upper end of each winding which must be observed for a proper operation of the circuit. In a prototype operating example, transistor Q1 was a 2N5087, transistor Q2 is a 2N1539 or a 2N277 or a 2N2082. Transformer 20 in the prototype was a universal plate output transformer such as a TA-9 produced by Essex STANCOR and the battery 27 can be two AA cells at 3 volts or a 9 volt radio battery. It is specifically contemplated by the inventors that much smaller transistors and transformer be used.

Figure 2:
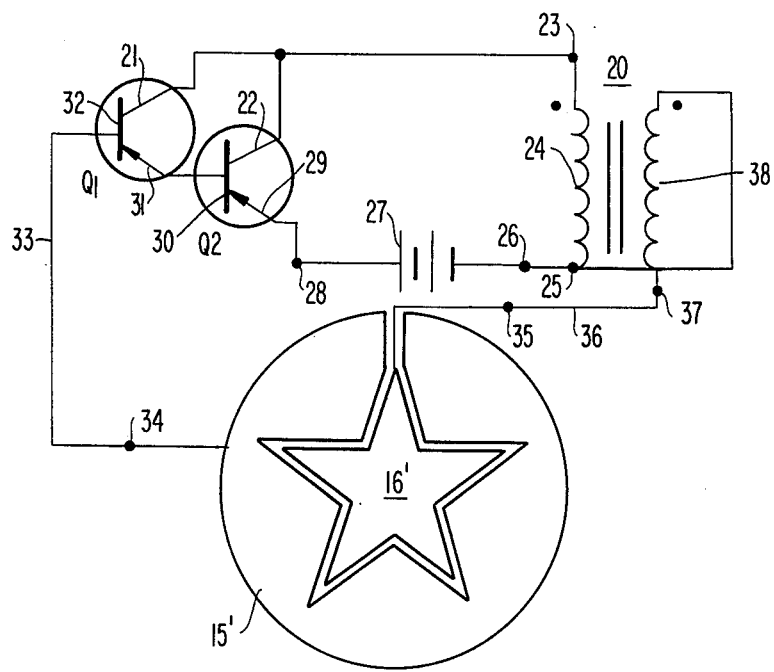
FIG. 2 is a detail schematic diagram of the invention in its most preferred form.
Figure 3C:
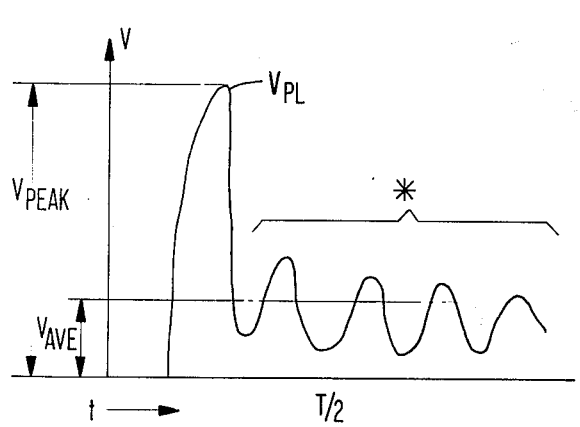
Figure 3C:
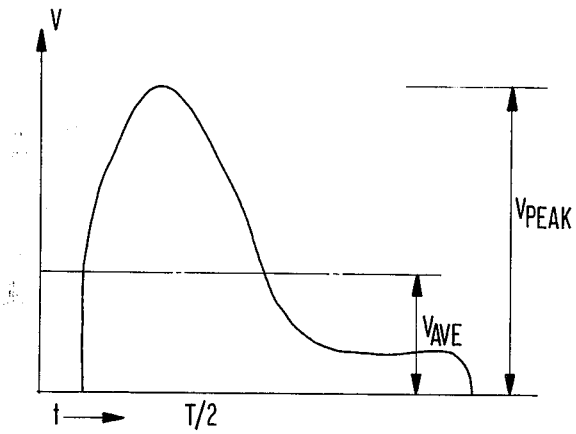
Figure 3C:
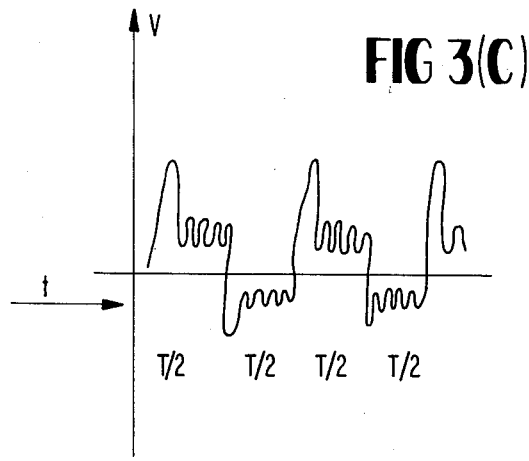

As shown in FIG. 2, the circuit is a Darlington common-emitter amplifier with (inverting) transformer coupled output. Since the common-emitter configuration provides both voltage gain and current gain while inverting the waveform, and the transformer provides additional voltage gain at the expense of current gain while again inverting the waveform, the output is in phase with the input with an overall power gain. Since the load provides feedback from the output to the input, it can provide negative resistance in the circuit depending on the magnitude of the feedback and gain of the amplifier. Attention is directed to chapters 15 through 17 of *Functional Circuits and Oscillators* (henceforth abbreviated as FCO) by Herbert J. Reich. Since the $h_{FE}$'s of the two transistors (in the prototype circuit) are respectively 250 to 800 and 35 to 70, and since further the gain of a Darlington is the product of the gains of its elements, the overall low-frequency gain is between the extremes of 9000 and 56000 with most likely region of 17000 to 28000. Furthermore over the region where the transistors are active the input resistance is greater than the $h_{ie}$ of the power transistor (at least a few hundred to a thousand ohms) times the $h_{FE}$ of the small signal transistor, thus, the input resistance is greater or equal to 50,000 ohms (worst case minimum). Thus negative resistance will be present (i.e., oscillation is possible) provided the feedback resistance (the load) is less than the input resistance multiplied by the gain, which is minimally $50,000 \times 9,000 = 450,000,000$. In other words, oscillation can occur if the load is less than 450 Megohms (worst case) (closer to 5 to 10 thousand Megohms (5,000,000,000) typically). This is assumed in the absence of capacitance, with capacitance present the feedback is increased, a mere 10 picofarads ($10 \times 10^{-12}$F.) provides the same reactance at the operating frequency range. Attention is now drawn to chapters 45 through 46 of FCO, in particular FIG. 157 and the last paragraph of chapter 46, and chapter 48. According to Reich, astable circuits can be generated from voltage-stable (open-circuit-stable) negative resistance elements by adding a small shunt capacitance (or using the internal capacitance of the element) and a series inductance. The inductance is provided in the present circuit by the leakage and primary inductances of the transformer. Depending on operating point and susceptance magnitudes, anything from square waves to sawtooth to pseudo-sine sawtooths may be generated. A rounded sawtooth is observed in the present circuit with very light loading (very little feedback). Attention is directed to chapter 57, chapters 72 through 75 of FCO and the article "Prevent Emitter-Follower Oscillation" in *Electronic Design* 13, June 21, 1976, pp. 110–113. Due to the leakage inductances from emitter to base, and from emitter to collectors, the space-charge and diffusion capacitances of both base-emitter junctions, the space-charge and diffusion capacitances of the collector-base junctions (magnified by the Miller effect) and the fact that all of these quantities (as well as incremental resistances of the transistors) vary with current, voltage, frequency or some combination of more than one of these, the input impedance and feedback impedance are both extremely complex functions (of more than one independent variable). An exact solution is therefore somewhat difficult to obtain. However, when the magnitude of the feedback is increased (slightly lower load impedance), a second mode of oscillation, sinusoidal, appears at a frequency within a couple of octaves of the primary frequency, whenever the instantaneous operating current is in a certain range. The output thus takes on its characteristic, and quite distinctive, waveform as shown in FIGS. 3(A), 3(B) and 3(C).

Figure 4:
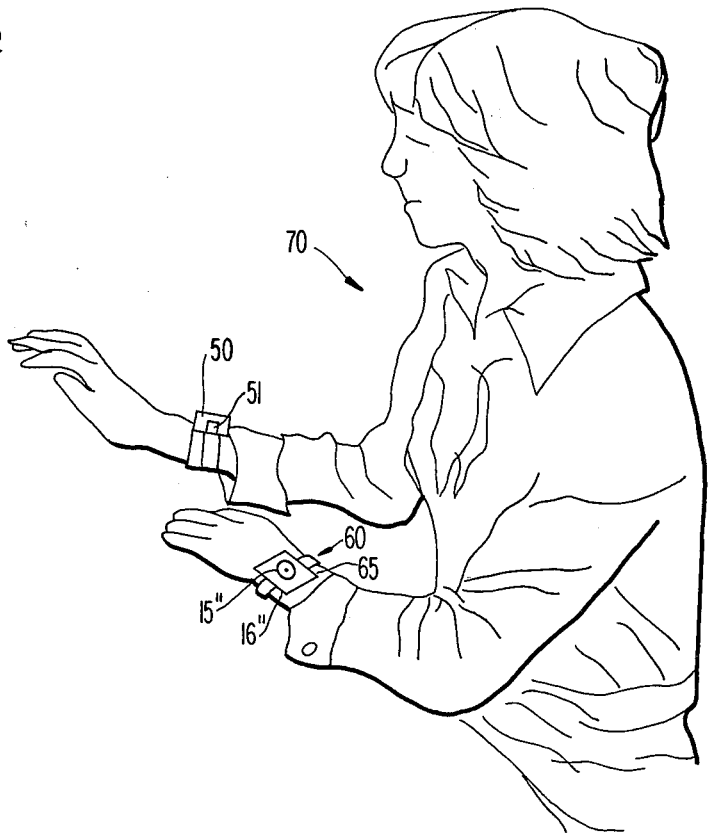
FIG. 4 is an illustration of the invention as applied to wrist units illustrating one form of the electrodes.

Copper as well as aluminum electrodes have been used. Decorative silver gold as well as other precious metal electrodes are in the contemplation of the inventors. In a highly preferred form of self-protective devices, particularly for use by women as an anti-rape device, the electrodes may be esthetic and in the form of decorative jewelry, as shown in FIG. 4 as wrist jewelry. Obviously the disguise of the electrodes can take many forms, and be secured or carried at other places on the person of the user.

Switch 13 may be in the form of an activating or arming switch which merely connects the battery 27 to either the mid-point 25 of transformer 20 or to emitter electrode 29. For example, a user may wish to disable or disarm the entire circuit while in social environments so as to assure that the shock produced is not applied to the body of an acquaintance or friend.

HARMONIC MODE OF OPERATION

As shown in FIGS. 3(A), 3(B) and 3(C), the various circuit forms of the device all exhibited a sinusoidal (harmonic oscillator) waveform component which is superimposed on a rounded sawtooth. The sawtooth component is produced by a relaxation oscillator mode of the circuit and is locked (synchronized) by the sinusoidal component, whenever the sinusoidal component is present, i.e., in the normal region of operation. Sinusoidal waveforms are produced by harmonic oscillators, which can be grouped into two categories. There are resonant harmonic oscillators and non-resonant harmonic oscillators. The non-resonant harmonic oscillators can be sub-divided further into null-network (including RC and RL bridges) oscillators, phase-shift oscillators, and time-delay (delay-line) oscillators. All of non-resonant harmonic oscillators are characterized by one or more feedback paths arranged such that at, at least one, frequency the phase angle around the feedback loop undergoes a total phase shift of $0 \pm 2\pi n$ radians ($0 \pm 360n°$) where $n$ is an integer. In the case of the phase shift oscillator, this is normally accomplished by the use of an inverting amplifier followed by a multi-section RC (or rarely RL) filter, with minimally two and usually three sections. The passive filter section then provides, at one frequency, an additional $\pm 180°$ of phase shift, which with the $-180°$ of the inverting amplifier gives a loop phase angle of 0° or $-360°$ (Of course the amplitude must be such that at the frequency(s) at which the phase angle meets the conditions set for it the loop gain is greater or equal to unity. The Nyquist stability criterion states for oscillation (harmonic) to occur there must be a frequency at which the loop gain is unity and the net phase angle is 0. If the loop gain is greater than unity, normally oscillations will increase in amplitude until, due to physical limitations of the amplifier, the loop gain has dropped to unity). In the circuits incorporating the invention, transformer 20 provides, essentially, signal inversion ($-180°$ phase shift) over a range of frequencies. Below the lower 3db frequency the phase angle is leading pure inversion, total angle of phase shift is less than −180°. At and above the upper 3db frequency the phase angle lags pure inversion resulting in a total phase shift of more than −180°. Since the phase shift is a continuous function of frequency there must be at least one frequency between these two limits at which the Nyquist criterion is satisfied, and by the nature of the physical limitations of the amplifier, if there is more than one, the lowest will be the frequency at which oscillation occurs. Since the input of the amplifier is somewhat lagging in phase reaching an angle of −45° at the fae (fae=$F_B$=5-15kHz) for the Ge alloy power, which decreases toward zero as frequency decreases; and the transformer 20 provides a lead of approximately +45° at its lower 3db frequency (around 20 Hertz for the transformers in question) which decreases toward zero as frequency increases, both phases referenced to pure inversion, the Nyquist criterion must be satisfied with the decade of frequency from about 20 Hertz upward to 200 Hertz. This agrees with the observed frequency of the harmonic (sinusoidal) component of the output. As shown in FIG. 3(C) the waveform was not symmetric about the time axis, the peak and average voltage differing. This was due to the use of single ended circuits in a relaxation configuration.

It was observed that this circuit with various substitutions of components and varying supply voltages will sometimes exhibit the sinusoidal component with clipping of the positive and/or negative peaks for one or more cycles due to saturation effects in the Darlington pair and/or the transformer core and/or cut-off of the Darlington pair. It was further observed that under the circumstances when this condition occurred the primary effect, an electrically induced shock, was not dilatoriously affected.

D.C. BIAS

The circuit is arranged such that positive biasing is derived through the resistive component of the load in a novel and highly efficacious manner. Germanium power transistors being relatively insensitive to D.C. levels and bias conditions, and the 2N5087 being a high gain transistor rated at minimum beta of 250 with a collector current of 0.1 through 10 milliamps, and a minimum beta of 200 at a collector current of 0.01 milliamp (10 micro-amp), the combination of the two as a Darlington pair functions quite adequately over an extremely large range of biasing conditions. However, silicon power transistors (which are much less preferred than the germanium types) are much more sensitive to biasing conditions. In the all silicon Darlington or pseudo-Darlington, using the 2N5087 as the input transistor Q1 there is no trouble in obtaining a minimum bias with large resistances in the feedback, however, the power transistor is prone to D.C. saturation as the feedback is increased (feedback resistance lowered). This can be overcome in one of two ways. The first is to balance the increasing positive bias with a fixed negative bias, accomplished by a large 1 to 10 Megohm resistor between 28 and 33 with the higher resistance values preferred. The second method is to insert a large electrolytic capacitor in series with the output terminal 34 (in line 33) and a standard 100 microfarad 10 volt polarized aluminum electrolytic capacitor was found to work acceptably. In this case, the necessary bias current was obtained through the leakage resistance of the capacitor, which passed the A.C. output unhindered. Non-electrolytic capacitors of high enough capacitance would be prohibitively bulky.

OTHER MODIFICATIONS

Other amplifiers would use biasing schemes appropriate to the type of amplifier. Norton current-differencing integrated solid state amplifiers could use the methods outlined above or, additionally, a fixed positive bias present at the inverting input. All three of the above methods would be suitable for standard differential input operational amplifiers, with the balancing D.C. level to the other input probably being best. Since it is not currently contemplated using amplifiers other than high gain transistors of the Darlington or pseudo-Darlington forms, preferably integrated circuit amplifiers, it is unnecessary to detail bias methods for other types of amplifiers.

DISCUSSION OF MEASUREMENTS

General Observation

The final circuit configuration, by configuration and its high gain, is sensitive to leakage admittance in the matter of initiating and maintaining oscillation. In a breadboard form, for example, it was possible to initiate oscillation by placing a hand or medium sized metal object within 2 or 3 inches of the layout, similarly twisting the output leads into a few turn 'gimmick' capacitor was sufficient to initiate oscillation. Occasionally, once oscillation began, it would be maintained even after conditions were returned to initial form.

The output waveform is, in contrast, relatively insensitive to loading effects. An 'unloaded' (FIG. 3(B)) waveform was observed with the scope alone or with the scope shunted by the VOM and/or a 7 Megohm ($7 \times 10^6$ ohms) linear potentiometer set to maximum resistance. In addition, it was observed to be insensitive to capacitive loading up to and including 1.5 nF (1500 pF). As the shunt resistance on the output was made lower in resistance, the output waveform changed in character until a 'loaded' waveform was reached. This waveform then remained qualitatively unchanged until output loading was enough to stop oscillation. Capacitive loading of the same amount as in the unloaded case again had no effect.

The waveforms in both the loaded and unloaded cases were observed to show, qualitatively, effectively no variation (i.e., no variation in shape) with changes in operating level or fundamental frequency.

QUANTITATIVE DATA

(a) Frequency

The fundamental frequency can be made to vary by adjusting the circuit elements or, to a lesser extent, by changing the output loading, normally, it is observed to lie within a decade of 100 Hz (10 to 1000 Hz). During operation, for the purposes currently being exploited, it is usually adjusted to stay within the octave 45 to 90 Hz.

(b) Voltage

Unloaded output voltages (average by rms weighting circuit, 50v and 250v scales primarily, meter set for A.C.), have been observed as low as approximately 10 volts and as high as 1.6kv (1600 volts) . . . 5Kv (5000 volts), however, outside of extreme areas of operation the averaged output voltage was observed to lie between 20 and 90 volts. This normal range is observed over a large range of loading conditions, from unloaded to just short of termination of oscillation. The peak to average voltage ratio was determined to be greater than 3 with the VOM and a neon bulb, and was observed to range from 4 to 7 with the scope, depending on circuit constants. The apparent disparity is understandable when one considers that a neon bulb is a gas discharge device which tends to act as a peak clipping element due to its non-linear resistance.

PERSONAL DEFENSE SYSTEM

In FIG. 4, a pair of the devices in the form of wrist jewelry 50 and 60 is illustrated in a de-energized state by a battery switch 51, for example (corresponding to switch 13 of FIG. 1). When the wearer 70 is about to enter any area where she deems to have the protection of the device from any would-be assailant, she merely turns the switch to on.

The object of the device is to induce a painful, but harmless, electric shock in the area of contact of a mammalian organism. The method used by existing devices (the 'cattleprod', Tingley et al., Cover, etc.) is to use high voltage, either direct or alternating current, to induce current flow in the contacted area. Damage, below the threshold necessary to cause burns, results from the current flow, and causes painful sensations since the sensory nerves react to the organic damage. Even though of a transient nature, the organic damage is not necessary and highly undesirable as this is wasteful of power, and critical of adjustment if more permanent damage is to be avoided.

The circuit of the present invention is normally quiescent and generates, under load, a waveform which breaks down the skin resistance (generally between a few thousand and a million or two ohms) and then couples directly into the sensory nerves (via this transient low resistance path), a signal having a frequency within the frequency passband of the nerves. This means much lower power can be used while achieving a greater, more painful or effective shock to thereby disable an assailant. Adjustment is much less critical as overload power levels to the nerves of several orders above what is normally presented by the present curcuit are still well below levels causing damage. Placement of contacts to a sensitive area of the body is not necessary, as an interference signal, coupled into the nervous system, affects to a lesser degree all areas connected to the same nerve trunk. This effect has been described by test subjects touching the output electrodes 15 and 16 with the index and middle fingers of one hand as "it crawled up my arm" and "I felt it up to my shoulder".

For passband of nerve we cite Holladay, David "Does the Action Potential of Nerve have a Mechanical Component? An Exploration of Models" Bachelor's Thesis, MIT 1976, Dept. of Electrical Engineering; Hill, A. V., 1933 "Wave Transmission as the Basis of Nerve Excitability", Cold Spring Harbor Symposium 1:146; Hodgkin, A. L. 1964 "Conduction of the Nervous Impulse" Charles Thomas, Springfield, Illinois.

The invention provides a minimal componentry power oscillator which functions by taking advantage of the non-ideal characteristics of the components, such as hysteresis and saturation in the inductive components and the phase/amplitude versus frequency response in the gain elements to produce stable, within a wide range, non-sinusoidal, low-frequency oscillations. The unique feedback configuration via the body of the assailant achieves a self-adjusting output. Because of the unique circuit configuration it does not require wetted contacts or electrodes to initiate oscillation.

Moreover, since the oscillator is quiescent (even when 'activated' or 'armed' by the closing of switch 13), the only power consumed is the leakage current of the output transistor Q2. In its preferred form, the only circuit components required are those shown in FIG. 2 so the circuit may be reduced to extremely small physical proportions or dimensions with transformer 20 and battery 27 being the largest components. The electrodes 15 and 16 may be deposited in various forms on a substrate and if crossovers are desired, a thin insulating layer may be used. Thus, in the circular electrode design shown in FIG. 4, electrode 15" is on colorful insulating layer L over electrode 16" and connected to the circuit carried in case 65 by leads not shown.

It is obvious that various other modifications and changes may be incorporated in the invention without departing from the spirit and scope thereof as set forth in the claims appended hereto.

We claim:

1. A personal defense system comprising in combination,
   a normally quiescent electrical circuit means which, when activated generates an electrical voltage waveform which has a relatively high voltage portion to break down the skin resistance of an assailant, and then couples directly to the assailant's sensory nerves a lower amplitude signal within the passband of the nerves of the human body, said lower amplitude signal being of sufficient amplitude to temporarily disable said assailant, and
   a pair of output electrodes connected to said normally quiescent electrical circuit means, said circuit means being activated only upon the presence of a portion of said assailant's body between said pair of output electrodes to produce between said electrodes said electrical voltage waveform.

2. The personal defense system defined in claim 1 wherein said waveform has an initial peak high voltage pulse followed by said signal within the passband of the nerves and wherein the ratio of said peak high voltage to the rms average of said signal within the passband of the nerves is in the range of 4 to 1 to about 7 to 1.

3. The personal defense system defined in claim 2 wherein the frequency of said signal within the passband of the nerves of the human body is from about 10 Hz to about 1000 Hz.

4. The personal defense system defined in claim 3 wherein the frequency of said signal is from about 20 Hz to about 200 Hz.

5. The personal defense system defined in claim 4 wherein said frequency of said signal is from about 45 Hz to about 90 Hz.

6. The personal defense system defined in claim 2 wherein the rms value of said signal is from about 10 volts to about 90 volts.

7. The personal defense system defined in claim 6 wherein the rms value of said signal is from about 20v to about 90v.

8. The personal defense system defined in claim 1 wherein said normally quiescent electrical circuit means includes an inverting high gain transistor amplifier, said inverting high gain transistor amplifier having an emitter-collector output circuit and a base-emitter input circuit, a source of unidirectional voltage, an inverting transformer having at least one winding connected in a first series circuit with said source of unidirectional voltage and said emitter-collector circuit, and at least one winding connected in a second series circuit feedback arrangement with said base-emitter input circuit and said pair of output electrodes connected in said second series circuit, said quiescent electrical circuit means being rendered oscillatory solely upon the application of a portion of the body of an assailant thereacross.

9. The personal defense system defined in claim 8 wherein said inverting transistor amplifier is a Darlington connected transistor pair.

10. The personal defense system defined in claim 9 wherein the output transistor of said Darlington pair is a germanium power transistor.

11. The personal defense system defined in claim 10 including an arming switch connected in series circuit with said source of unidirectional voltage.

12. The personal defense system defined in claim 1 including a plurality of said normally quiescent electrical circuit means and a corresponding plurality of output electrodes adapted to be secured secured at various locations on the person of the user so that at least one of said quiescent circuit means is activated by an assailant upon contacting a pair of said electrodes.

13. The personal defense system defined in claim 12 wherein at least one of said electrode pairs is in the form of decorative jewelry.

14. The personal defense system defined in claim 1 wherein said pair of electrodes are on a common substrate and disguised in the form of jewelry.

15. The personal defense system defined in claim 1 wherein said normally quiescent circuit means includes a direct current battery, an oscillator which consists of an inverting transformer having a primary winding and a feedback winding, an inverting transistor amplifier having a Darlington connected transistor pair with a germanium power output transistor conductor means connecting the primary winding of said transformer said battery and the emitter-collector circuit of said germanium output transistor in a series circuit, and further conductor means connecting said pair of electrodes, said feedback winding said battery and the emitter electrode of said germanium output transistor and the other transistor of said Darlington connected pair in a further series circuit.

16. A method of applying electrical energy to an assailant which electrical energy is below the threshold necessary to cause organic damage but sufficient to introduce a painful and disabling shock to an assailant, which comprises,
    causing the lowering of the skin resistance of the assailant with an initial relatively high voltage pulse of short duration to create a transient low resistance electrical path and then
    coupling a sequence of oscillatory voltage pulses of relatively lower amplitude directly into the sensory nerves of the assailant via the transient low resistance electrical path, said sequence of oscillatory voltage pulses being a signal within the passband of the nerves and of sufficient amplitude to temporarily disable the assailant.

17. The method defined in claim 16 wherein the ratio of amplitudes of said initial voltage pulse and said sequence of oscillatory pulses is in the range of from about 4 to 1 to about 7 to 1.

18. The method defined in claim 16 wherein said sequence of oscillatory pulses numbers from about four to about six.

19. The method defined in claim 16 wherein there is provided an armed, normally quiescent, electrical circuit for producing said pulses, said electrical circuit having a pair of electrodes adapted to contact an area of the body of an assailant,
    the further step of activating said circuit by placing said electrodes in contact with an area of the body of an assailant.

20. The method defined in claim 19 wherein said circuit is an oscillatory circuit having a feedback transformer, with a feedback winding in series circuit with said pair of electrodes and that portion of the body of the assailant completing the feedback circuit for said oscillatory circuit, the energy of said initial relatively high voltage pulse being absorbed and attenuated by a portion of the body of said assailant and the remaining portion thereof constituting feedback energy for said oscillatory circuit.

21. The method of temporarily disabling a mammalian organism which comprises,
    applying a pair of electrodes to the exterior skin surface of said mammalian organism, applying through said electrodes an electrical pulse to the body of the organism to form a transient low resistance path without organic damage and then,
    coupling a sequence of lower amplitude oscillatory pulses via said low resistance path which have a frequency within the frequency passband of the nerves of the organism, said lower amplitude pulses being of sufficient amplitude to achieve the disablement of the mammalian organism.

22. The method of introducing electrical energy to the human body which comprises generating a low power electrical signal having a waveform which has at least one relatively low amplitude voltage component which has a frequency within the passband of the nerves of the human body,
    and simultaneously with the generation thereof applying via a pair of spaced apart electrodes said at least one relatively low amplitude voltage component which is within the passband of the human body to the human body, said low voltage component being generated only as a result of said spaced electrodes contacting said human body.

23. The method defined in claim 22 wherein said waveform includes a large amplitude pulse preceding said relatively low amplitude component and said large amplitude pulse creates a low resistance path for said relatively low amplitude component of said waveform.

24. The method defined in claim 23 wherein said pair of human body contacting electrodes and the said generated electrical waveform are applied to the exterior of the human body via said body contacting electrodes.

25. The method defined in claim 22 wherein said frequency is from about 10 to about 1000 Hz.

26. The method defined in claim 22 wherein said frequency is from about 20 to about 200 Hz.

27. The method defined in claim 22 wherein said frequency is from about 45 to about 90 Hz.

28. The method defined in claim 22 wherein said relatively low amplitude voltage component has an average value of from about 10 to about 90 volts rms.

29. The method defined in claim 28 wherein the said frequency is from about 10 to about 1000 Hz.

30. The method defined in claim 29 wherein said frequency is from about 20 to about 200 Hz.

31. The method defined in claim 30 wherein said frequency is from about 45 to about 90 Hz.

32. The method defined in claim 22 wherein said relatively low amplitude voltage component has an average rms value of from about 20 to about 90 volts rms.

* * * * *